US00PP25163P2

(12) United States Plant Patent
Isobe

(10) Patent No.: US PP25,163 P2
(45) Date of Patent: Dec. 9, 2014

(54) ***PETUNIA* PLANT NAMED 'SUNSURF SKYTATSU'**

(50) Latin Name: *Petunia×hybrida*
Varietal Denomination: Sunsurf Skytatsu

(71) Applicant: Yasuko Isobe, Shiga (JP)

(72) Inventor: Yasuko Isobe, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 105 days.

(21) Appl. No.: 13/815,131

(22) Filed: Jan. 31, 2013

(51) Int. Cl.
*A01H 5/00* (2006.01)

(52) U.S. Cl.
USPC ..... Plt./356.2

(58) Field of Classification Search
USPC ..... Plt./356, 356.2
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'Sunsurf Skytatsu', characterized by its semi-upright to trailing plant habit; vigorous growth habit; freely branching habit; early and freely flowering habit; long flowering period; large violet-colored flowers; and good garden performance.

1 Drawing Sheet

Botanical designation: *Petunia×hybrida*.
Cultivar denomination: 'SUNSURF SKYTATSU'.

BACKGROUND OF THE INVENTION

The present invention relates to a new and distinct cultivar of *Petunia* plant, botanically known as *Petunia×hybrida* and hereinafter referred to by the name 'Sunsurf Skytatsu'.

The new *Petunia* plant is a product of a planned breeding program conducted by the Inventor in Higashiomi, Shiga, Japan. The objective of the breeding program is to create new freely branching and freely flowering *Petunia* plants with a semi-upright to trailing plant habit and numerous large attractive flowers.

The new *Petunia* plant originated from a cross-pollination made by the Inventor in July, 2009 in Higashiomi, Shiga, Japan of a proprietary selection of *Petunia×hybrida* identified as code number BOSK, not patented, as the female, or seed, parent with a proprietary selection of *Petunia×hybrida* identified as code number Px2613-01, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in June, 2010.

Asexual reproduction of the new *Petunia* plant by terminal cuttings in a controlled greenhouse environment in Higashiomi, Shiga, Japan since June, 2010 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunsurf Skytatsu'. These characteristics in combination distinguish 'Sunsurf Skytatsu' as a new and distinct *Petunia* plant:

1. Semi-upright to trailing plant habit.
2. Vigorous growth habit.
3. Freely branching habit.
4. Early and freely flowering habit.
5. Long flowering period.
6. Large violet-colored flowers.
7. Good garden performance.

Plants of the new *Petunia* can be compared to plants of the female parent selection. Plants of the new *Petunia* differ primarily from plants of the female parent selection in the following characteristics:

1. Plants of the new *Petunia* are larger than plants of the female parent selection.
2. Plants of the new *Petunia* are more freely branching than plants of the female parent selection.
3. Plants of the new *Petunia* and the female parent selection differ in flower throat color as plants of the female parent selection have white-colored flower throats.

Plants of the new *Petunia* can be compared to plants of the male parent selection. Plants of the new *Petunia* differ primarily from plants of the male parent selection in the following characteristics:

1. Plants of the new *Petunia* are larger than plants of the male parent selection.
2. Plants of the new *Petunia* are more freely branching than plants of the male parent selection.
3. Plants of the new *Petunia* and the male parent selection differ in flower throat color as plants of the male parent selection have bluish purple-colored flower throats.

Plants of the new *Petunia* can also be compared to plants of the *Petunia* 'KEllavbu', disclosed in U.S. Plant Pat. No. 13,542. In side-by-side comparisons conducted in Higashiomi, Shiga, Japan, plants of the new *Petunia* and 'KEllavbu' differed primarily in the following characteristics:

1. Plants of the new *Petunia* were taller and narrower than plants of 'KEllavbu'.
2. Plants of the new *Petunia* were more upright than and not as spreading as plants of 'KEllavbu'.

3. Plants of the new *Petunia* had longer internodes than plants of 'KEllavbu'.
4. Plants of the new *Petunia* were more freely flowering than plants of 'KEllavbu'.
5. Plants of the new *Petunia* had smaller flowers than plants of 'KEllavbu'.
6. Petal margins of plants of the new *Petunia* were more undulate than petal margins of plants of 'KEllavbu'.
7. Plants of the new *Petunia* and 'KEllavbu' differed in flower color as plants of 'KEllavbu' had lighter violet-colored flowers.
8. Plants of the new *Petunia* had longer peduncles than plants of 'KEllavbu'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurf Skytatsu' grown in a container.

The photograph at the bottom of the sheet is a close-up view of a typical flowering plant of 'Sunsurf Skytatsu'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Petunia×hybrida* 'Sunsurf Skytatsu'.

Parentage:

*Female, or seed, parent*.—Proprietary selection of *Petunia×hybrida* identified as code number BOSK, not patented.

*Male, or pollen, parent*.—Proprietary selection of *Petunia×hybrida* identified as code number Px2613-01, not patented.

Propagation:

*Type*.—By terminal cuttings.

*Time to initiate roots, summer and winter*.—About one week at temperatures of about 15° C. to 20° C.

*Time to produce a rooted young plant, summer and winter*.—About three weeks at temperatures of about 15° C. to 20° C.

*Root description*.—Fibrous; white in color.

*Rooting habit*.—Freely branching; dense.

Plant description:

*Plant form and growth habit*.—Semi-upright to trailing plant habit; freely branching habit with numerous lateral branches developing per plant; pinching enhances lateral branch development; vigorous growth habit.

*Plant height*.—About 69.5 cm.

*Plant diameter*.—About 33.5 cm.

Lateral branch description:

*Length*.—About 28.8 cm.

*Diameter*.—About 2.7 mm.

*Internode length*.—About 2.75 cm.

*Strength*.—Strong, flexible.

*Aspect*.—Upright to outwardly.

*Texture*.—Pubescent.

*Color*.—Close to 144C.

Foliage description:

*Arrangement*.—Alternate, simple.

*Length*.—About 3.9 cm.

*Width*.—About 2 cm.

*Shape*.—Elliptic.

*Apex*.—Broadly acute.

*Base*.—Obtuse.

*Margin*.—Entire.

*Texture, upper and lower surfaces*.—Pubescent.

*Venation pattern*.—Pinnate; reticulate.

*Color*.—Developing leaves, upper surface: Close to 144A. Developing leaves, lower surface: Close to 144B. Fully expanded leaves, upper surface: Close to 143A; venation, close to 144C. Fully expanded leaves, lower surface: Close to 143C; venation, close to 144D.

*Petioles*.—Length: About 4.4 mm. Diameter: About 2.7 mm. Texture, upper and lower surfaces: Pubescent. Color, upper and lower surfaces: Close to 144C.

Flower description:

*Flower arrangement and habit*.—Single salverform flowers arising from upper leaf axils; freely flowering habit with usually about 83 flowers developing per plant; flowers face upright to outwardly.

*Fragrance*.—None detected.

*Natural flowering season*.—Early flowering habit, plants of the new *Petunia* initiate and develop flowers about two weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower diameter*.—About 5.2 cm.

*Flower length (depth)*.—About 3.9 cm.

*Throat diameter*.—About 1.1 cm.

*Tube diameter, base*.—About 3.5 mm.

*Tube length*.—About 2.75 cm.

*Flower buds*.—Length: About 3.8 cm. Diameter: About 6.6 mm. Shape: Cylindrical. Color: Close to N82A.

*Corolla*.—Arrangement: Five petals fused at the base and opening into a flared trumpet. Petal length from throat: About 2.3 cm. Petal width: About 2.4 cm. Petal shape: Spatulate. Petal apex: Mucronate. Petal margin: Entire, undulate. Petal texture, upper surface: Smooth, glabrous; velvety. Petal texture, lower surface: Smooth, glabrous. Throat texture: Smooth, glabrous. Tube texture: Pubescent. Color: Petal, when opening, upper surface: Close to N88A. Petal, when opening, lower surface: Close to N88C. Petal, fully opened, upper surface: Close to N88B; venation, close to N88B; color becoming closer to N88C with development. Petal, fully opened, lower surface: Close to N87D; venation, close to N87D. Throat: Close to N88C; venation, close to N88A. Tube: Close to N87C; venation, close to N87C.

*Calyx*.—Arrangement: One star-shaped calyx tube with five sepals in a single whorl and fused at the base. Sepal length: About 1.4 cm. Sepal width: About 4.8 mm. Sepal shape: Narrowly elliptic. Sepal apex: Obtuse. Sepal margin: Entire. Sepal texture, upper and lower surfaces: Pubescent. Color: Developing and fully developed sepals, upper surface: Close to 143A. Developing and fully developed sepals, lower surface: Close to 143B.

*Peduncles*.—Length: About 3 cm. Diameter: About 1.3 mm. Strength: Strong. Aspect: Upright to outwardly. Texture: Pubescent. Color: Close to 144B.

*Reproductive organs*.—Stamens: Quantity per flower: Five. Stamen length: About 1.6 cm to 2 cm. Anther shape: Ellipsoidal. Anther size: About 1.6 mm by 2 mm. Anther color: Close to 4D. Pollen amount: Abundant. Pollen color: Close to 4D. Pistils: Quantity per flower: One. Pistil length: About 2.2 cm. Style color: Close to 145D. Stigma shape: Transversely ellipsoidal. Stigma color: Close to 144A. Ovary color: Close to 145A. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurf Skytatsu' as illustrated and described.

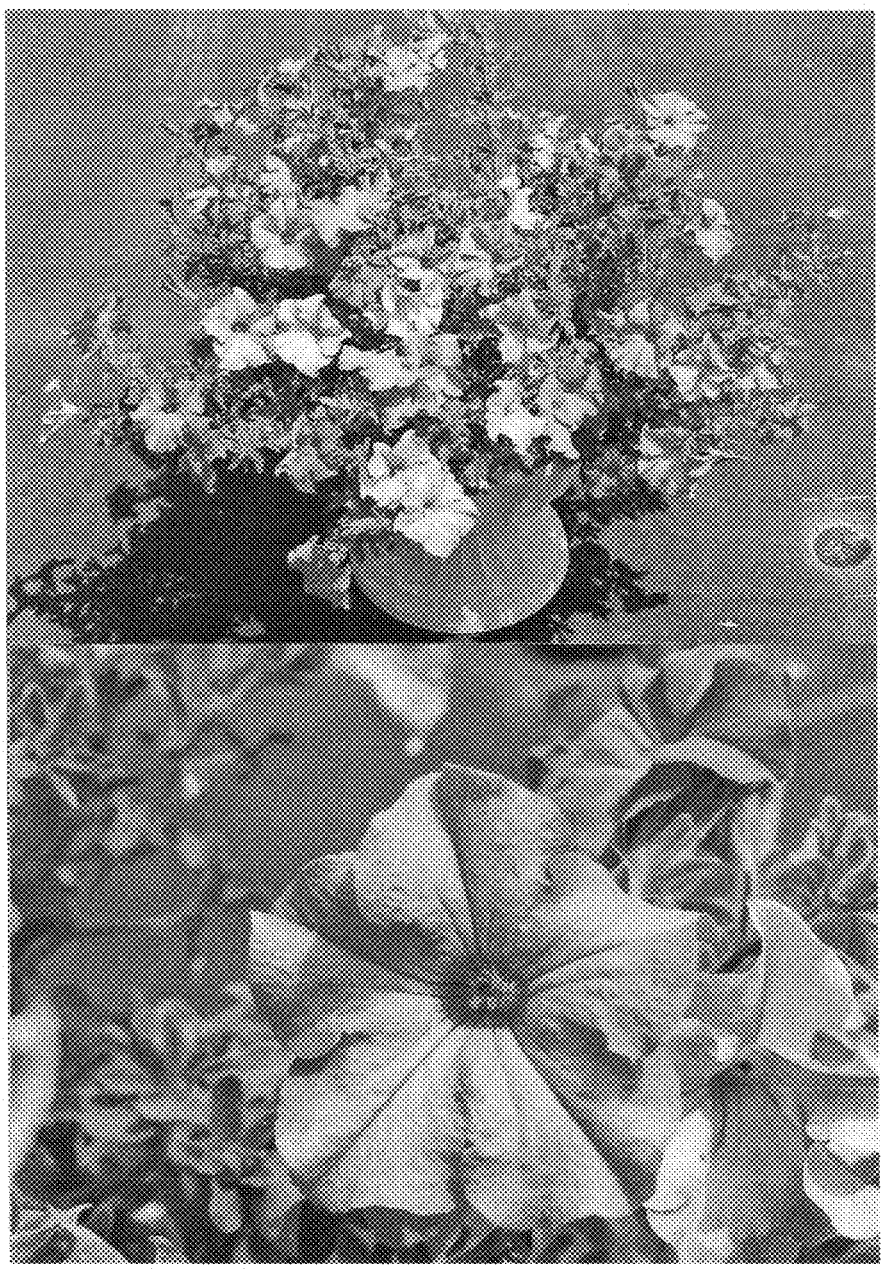

* * * * *